(12) United States Patent
Van Zutphen et al.

(10) Patent No.: US 9,447,128 B2
(45) Date of Patent: Sep. 20, 2016

(54) METHOD FOR PREPARING TRISHYDROXYMETHYL PHOSPHINE

(71) Applicant: MAGPIE POLYMERS, Saint Pierre les Nemours (FR)

(72) Inventors: Steven Van Zutphen, Bourron Marlotte (FR); Vladica Bocokic, Avon (FR)

(73) Assignee: MAGPIE POLYMERS, Saint Pierre les Nemours (FR)

( * ) Notice: Subject to any disclaimer, the term of this patent is extended or adjusted under 35 U.S.C. 154(b) by 0 days.

(21) Appl. No.: 15/023,571

(22) PCT Filed: Sep. 17, 2014

(86) PCT No.: PCT/IB2014/064579
§ 371 (c)(1),
(2) Date: Mar. 21, 2016

(87) PCT Pub. No.: WO2015/040549
PCT Pub. Date: Mar. 26, 2015

(65) Prior Publication Data
US 2016/0207947 A1    Jul. 21, 2016

(30) Foreign Application Priority Data
Sep. 19, 2013  (EP) .................................... 13306277

(51) Int. Cl.
*C07F 9/28* (2006.01)
*C07F 9/50* (2006.01)

(52) U.S. Cl.
CPC .................. *C07F 9/5086* (2013.01)

(58) Field of Classification Search
CPC ................................................... C07F 9/5086
USPC ............................................................ 568/13
See application file for complete search history.

(56) References Cited

U.S. PATENT DOCUMENTS

| | | | |
|---|---|---|---|
| 4,157,313 A | 6/1979 | Conan et al. | |
| 4,163,760 A | 8/1979 | Elsner et al. | |
| 5,284,555 A | 2/1994 | Hoye et al. | |
| 8,268,068 B2 | 9/2012 | Van Zutphen et al. | |
| 2010/0068143 A1 | 3/2010 | Van Zutphen et al. | |
| 2012/0238527 A1 | 9/2012 | Marchal et al. | |

FOREIGN PATENT DOCUMENTS

| | | |
|---|---|---|
| EP | 2 230 244 A1 | 9/2010 |
| WO | 00/024752 A1 | 5/2000 |
| WO | 01/81635 A1 | 11/2001 |

OTHER PUBLICATIONS

Dec. 23, 2014 International Search Report issued in International Patent Application No. PCT/IB2014/064579.

(Continued)

*Primary Examiner* — Porfirio Nazario Gonzalez
(74) *Attorney, Agent, or Firm* — Oliff PLC (57) ABSTRACT

A method for preparing trishydroxymethyl phosphine from tetrakishydroxymethyl phosphonium salt, the method including at least the steps of continuously feeding a first reaction chamber with, from one hand, at least one tetrakishydroxymethyl phosphonium salt and, from another hand, at least one base, under conditions suitable for a reaction of the tetrakishydroxymethyl phosphonium salt(s) with the base(s), to form a mixture of trishydroxymethyl phosphine and formaldehyde; and continuously removing the formaldehyde.

17 Claims, 1 Drawing Sheet

(56) References Cited

OTHER PUBLICATIONS

Philip Kisanga et al; "The synthesis of 2,6,7-trioxa-1,4 diphosphabicyclo [2.2.2]octane revisited: the synthesis of 2,6,7 triphenyl-2N, 6N, 7N-triaza-1,4-diphosphabicyclo [2.2.2]octane and the synthesis of 1-lambda^ 5-phosphiranol;" Heteroatom Chemistry; 2001; vol. 12; No. 2; pp. 114-117.

James W. Ellis et al; "Water-soluble tris(hydroxymethyl)phosphine complexes with nickel, palladium, and platinum. Crystal structure of [Pd{P(CH2OH)3}4].CH3OH;" Inorganic Chemistry;1992; vol. 31; No. 14; pp. 3026-3031.

S. J. Addison; "The functionalisation of wool by tris(hydroxymethyl)phosphine for metal ion recovery;" University of Waikato; 2009, pp. 1-71.

P.G. Pringle: "Tris(hydroxymethyl)phosphine platinum metal complexes;" Platinum Metals Rev.; 1990; vol. 34; No. 2; pp. 74-76.

Dmitry V. Moiseev et al; "Chemistry and stereochemistry of the interaction of the water-soluble phosphine [HO (CH2)3]3P with cinnamaldehyde in aqueous media;" Inorganic Chemistry; 2007; vol. 46; No. 11; pp. 4704-4712.

Martin Grayson; "Phosphonium compounds. III. Mechanism of hydroxide cleavage of tetrakis(hydroxymethyl) phosphonium chloride;" Journal American Chemical Society; Jan. 5, 1963; vol. 85, pp. 79-83.

METHOD FOR PREPARING TRISHYDROXYMETHYL PHOSPHINE

The present invention relates to a method for preparing trishydroxymethyl phosphine (THP) and using it to make phosphines or phosphine containing functionalized materials. More specifically, the invention relates to a novel method for preparing trishydroxymethyl phosphine from a tetrakishydroxymethyl phosphonium salt.

Trialkyl phosphines are used in numerous fields. Indeed, phosphines, phosphine oxides, phosphine sulphides, phosphine selenides, phosphine tellurides or iminophosphoranes are used in the preparation of a great diversity of ligands implemented in catalytic agents used for specialty and fine chemicals production. These compounds have also been incorporated in different polymeric materials, by means of the functionalization of polysiloxane, polystyrene or polyethylene glycol type polymers.

Disadvantages of the usual methods for preparing trialkyl phosphines is that they requires the use of $PH_3$ (phosphine) or $PCl_3$ (Phosphorus trichloride) and related $PR_{3-x}H_x$ and $PR_{3-x}Cl_x$ compounds where x=1 or 2 (see for instance, EP 2 230 244 and U.S. Pat. No. 8,268,068). Those compounds are dangerous reagents, highly toxic, highly reactive in air and water, and therefore highly difficult to handle, in particular under ambient conditions. Moreover, $PCl_3$ or $PH_3$ chemistry is strictly anhydrous and must be carried out using dry, oxygen free organic solvents, often at low temperatures (see for instance, U.S. Pat. No. 4,163,760 and U.S. Pat. No. 5,284,555). Accordingly, those reactive phosphorus compounds, when used in large scale in industry for the preparation of phosphine, are used in dedicated facilities that have required large capital investment prior to being functional.

Thus, there is a need for safer, as well as cheaper, methods for preparing trialkyl phosphines.

It is known that it is possible to prepare trialkylphosphines of the type $PR^1R^2R^3$ from trishydroxymethyl phosphine (THP) by reacting it with electrophiles, Indeed, THP (or $P(CH_2OH)_3$) and related $PR_{3-x}(CH_2OH)_x$ compounds with x=1 or 2 form an attractive alternative to the above mentioned chemistry involving $PH_3$ or $PCl_3$. THP and related $PR_{3-x}(CH_2OH)_x$ compounds are species that are stable in air and water and can be handled readily both in laboratory and in chemical industrial environment.

Also, THP may be used to functionalize polymers to yield phosphine containing polymers. Hence, THP can be used to functionalize polymer or resin beads, which find multiple uses in different fields, such as water and liquid-waste treatment.

Tris(hydroxymethyl)phosphine can also be grafted onto a silica polysiloxane support (U.S. Pat. No. 4,157,313) to be used for complexing metal atoms. These compounds can further be used for the production of metal capturing particles as described, for example, by S. J. Addison in "*The functionalisation of wool by tris(hydroxymethyl)phosphine for metal ion recovery*" (Thesis, University of Waikato, 2009). Polymeric compounds prepared from tris(hydroxymethyl)phosphine as a starting material have also been proposed in EP 2 230 244.

However, the synthesis of such organophosphorus compounds from THP and related $PR_{3-x}(CH_2OH)_x$ with x=1 or 2 is made difficult by the formation of side-products, typically oxidation products of the starting materials, the intermediates and the final products. This makes that many of the specialty organophosphorus compounds available commercially are expensive and available in small amounts. Traditionally synthesis and handling of compounds derived from $PH_3$ and $PCl_3$ has been carried out in a controlled environment, for example under nitrogen atmosphere, using small batch reactors so that there is accurate control of the stoichiometry, reaction temperature and mixing quality (Ellis et al., Inorg. Chem., 1992, 31, 3026 and Pringle et al., Platinum Metals Rev., 1990, 34, 2, 74). On such small scale such a high degree of control over reaction parameters and the purification of intermediates is possible. However, production at an industrial scale proves to be difficult.

The production and use of THP are inherently too limited by the difficulty to obtain this compound under a pure and stable form.

THP can be made in one-step reaction from a phosphonium salt, such as tetrakishydroxymethyl phosphonium sulphate (THPS) or tetrakishydroxymethyl phosphonium chloride (THPC). However, problems related to THP synthesis and its industrial employability are lack of control over the reaction in a classical reactor and the need for purification steps.

Woodward et al. have demonstrated that it is possible to synthesize mixture of phosphines from an in situ produced THP in a batch process (WO 00/024752 A1). However, the pH value varied between 6 and 8, leading thus inevitably to formation of a certain quantity of the phosphine oxide, which was always detected in the reaction mixture. Moreover, the final product (phosphine) was never obtained pure but in a mixture of phosphines that had to be tediously separated from one another.

It is also known in the art (US 2012/238527) that THPC can be transformed into THP to subsequently yield trialkylphosphines. Importantly, sulfite is used therein to remove the formaldehyde driving the transformation. Furthermore, in the disclosed embodiment, the transformations are carried out under inert atmosphere in batch conditions. Both of which could pose a serious difficulty in transforming the reaction into a cheap and scalable industrial process.

For the preparation of THP from a corresponding phosphonium salt, the control of the pH of the reaction, of the uniformity of the pH, of the stoichiometry of the reactants, and of the degree of mixing of the reactants, are among the parameters to set in order to obtain a high-quality product with a high yield. It proves to be a challenging task under usual, batch, reaction conditions, as was seen above and shown in the work of Kisanga et al., (Heteroatom Chemistry, 2001, 12, 2:114) and of Moiseev et al. (Inorg. Chem., 2007, 46:4704). Also, for the preparation of THP, avoiding oxidation reactions, which lead to side-product forming (Trishydroxymethyl phosphine oxide: THPO), is important to insure a high-quality product that can be stably stored for long periods of time, or used in subsequent steps.

For instance, if the stoichiometry of the reaction is not respected, the reaction between a base, such as NaOH, and a tetrakishydroxymethyl phosphonium salt to yield THP can instead give the undesired formation of THPO, but also a rapid liberation of hydrogen gas if the hydroxyl ions are present in an excess, even in a local one (M. Grayson, J. Am. Chem. Soc., 1963, 79-83). Such liberation of flammable and explosive gas on a large scale is a serious hazard.

Furthermore, during the transformation of a tetrakishydroxymethyl phosphonium salt into THP, for each mole of phosphine produced, a mole of formaldehyde is also formed. The formaldehyde is a dangerous chemical compound and a potential carcinogenic agent. It is also an undesired product. If present with THP, it may negatively affect subsequent reactions of THP with other reactants.

In addition, formaldehyde can react with THP to form hemi-acetal species with slightly lower reactivity compared to THP. When a nucleophile such as $NH_3$ is added, formaldehyde will favor the formation of the thermodynamic product 1,3,5-triaza-7-phosphaadamantane. If formaldehyde is not removed, the starting material tetrakishydroxymethyl phosphonium salt can also form back over time.

Thus, there remains a need for preparing trialkyl phosphines by means of safer and cheaper methods.

There is also a need for a method of preparation of THP to obtain a high-quality product in high yield.

There is also a need for a method of preparation of THP allowing the easy and cost-effective removal of side-products, such as formaldehyde.

Further, it remains a need to reduce toxicity risks associated with THP production.

The present invention has for purpose to meet these needs.

According to a first embodiment, the present invention relates to a method for preparing trishydroxymethyl phosphine from tetrakishydroxymethyl phosphonium salt, said method comprising at least the steps of continuously feeding a first reaction chamber with, from one hand, at least one tetrakishydroxymethyl phosphonium salt and, from another hand, at least one base, under conditions suitable for a reaction of said tetrakishydroxymethyl phosphonium salt(s) with said base(s), to form a mixture of trishydroxymethyl phosphine and formaldehyde; and continuously removing said formaldehyde.

Indeed, the inventors have established, as illustrated in the Examples, that it is possible to continuously remove side-products, and in particular formaldehyde, formed concomitantly during the obtaining of THP following a reaction between a tetrakishydroxymethyl phosphonium salt and a base, so as to obtain a substantial highly-pure THP in a high yield.

Also, it was established that the THP so-obtained can be continuously reacted with different reactants so as to obtain, on large scale and at reduced cost, a wide range of phosphines and phosphine containing polymers and materials.

By continuously removing formaldehyde, a high quality and highly pure stable THP is produced continuously and on a large scale. There is no need for further purification.

Advantageously, with the method of the invention, more than 98% of the formaldehyde is removed, preferably more than 99% of the formaldehyde is removed and more preferably all the formaldehyde is removed.

Further, it was established that a micro-reactor technology can be combined with continuous side-products removal to obtain THP, and to make a wide range of phosphines and phosphine containing polymers and materials available on large scale cheaply and safely. With the microreactor technology, the control of reactants stoichiometry and mixing may be easily performed in the production process, and the risk of formation of hydrogen gas may be avoided or substantially reduced.

Therefore, one of the advantages of the present invention is the reduced risks for the operator's health and safety.

Moreover, the tetrakishydroxymethyl phosphonium salt(s) and the base(s) to be used within the invention are preferably solubilized in an aqueous solvent, and preferably in water.

Therefore, one of the other advantages of the invention is that it may be purely water-based, thus eliminating the use of any organic, flammable or toxic solvent.

According to one of the advantages of the invention, it is possible to prepare THP at an industrial scale, in highly-pure form, not requiring additional purification for further uses.

According to another of the advantages of the methods of the invention, is that they may be run with standard equipment at low costs.

Other features and advantages of the invention will emerge more clearly from the description and examples that follow.

A method of the invention for preparing trishydroxymethyl phosphine from tetrakishydroxymethyl phosphonium salt comprises at least the steps of continuously feeding a first reaction chamber with, from one hand, at least one tetrakishydroxymethyl phosphonium salt and, from another hand, at least one base, under conditions suitable for a reaction of said tetrakishydroxymethyl phosphonium salt(s) with said base(s), to form a mixture of trishydroxymethyl phosphine and formaldehyde; and continuously removing said formaldehyde.

According to one embodiment, a tetrakishydroxymethyl phosphonium salt suitable for the invention may be chosen from tetrakishydroxymethyl phosphonium sulphate (THPS), tetrakishydroxymethyl phosphonium chloride (THPC), and mixtures thereof.

A tetrakishydroxymethyl phosphonium salt may be preferably solubilized into an aqueous solvent, and more preferably in water.

The solvents may also include alcohols, for example chosen from methanol, ethanol, 1-propanol, 2-propanol, tetrahydrofurane, dimethylsolfoxide, dimethylformamide, dimethylacetamide, pure or mixed with water in any ratio solvent/water.

The concentrations of tetrakishydroxymethyl phosphonium salt may vary from 5.0 mol/l to 2.0 ml/l.

According to one embodiment, a base suitable for the invention may be chosen from NaOH, $CaCO_3$, KOH, $Na_2CO_3$, CaO, $Ca(OH)_2$, and non-nucleophilic amines, such as triethylamine or diisopropylethylamine (of the formula $R_3N$, where R cannot be H), and preferably from NaOH, $CaCO_3$, and non-nucleophilic amines.

The time of residence of the tetrakishydroxymethyl phosphonium salt(s) and of the base(s) in the reaction chamber is set so as to allow a complete reaction between those compounds. The time of residence may vary according to different parameters, such as, and in non-limiting manner, the temperature of the reaction, the volume (diameter/length) of the chamber, the concentrations of the compounds to be reacted, the flow of the compounds into the chamber. The time of residence may set by a skilled man through different routine experiments.

In one embodiment, the time of residence of the tetrakishydroxymethyl phosphonium salt(s) and the base(s) in the first reaction chamber may range from 0.5 to 30 minutes.

The pH is a parameter, the adjustment of which may help to provide THP of very high quality.

Indeed, at low pH, namely below 5, the equilibrium of the reaction is shifted towards the tetrakishydroxymethyl phosphonium salt(s), while at a higher pH, namely above 5, the equilibrium of the reaction is shifted towards the formation of THP, but at still higher pH, namely above 7.5, the side-product oxide THP tends to form in significant amounts.

Therefore, according to one embodiment, the pH of the reaction in the reaction chamber may be brought to a pH set ranging from 6.5 to 7.5, or preferably ranging from 6.9 to 7.0.

The pH of the reaction may be controlled and adjusted by any means known in the art. For example, the pH in the first reaction chamber may be continuously monitored by an electrode connected to the pump that automatically doses the base to the chamber depending on the current and the desired pH value. Such systems for automatic titration and pH-value adjustment are commercially readily available.

According to one embodiment, the reaction in the first reaction chamber may be kept at a constant temperature. Preferably, the reaction is brought to a temperature ranging from 20° C. to 50° C., preferably between 30° C. and 40° C., in particular using a thermostatic bath into which the reaction chamber is immersed.

The control of temperature may be carried out by any means known in the art. For example, to keep the reaction at the desired temperature, the chamber may be submerged in an externally cooled or heated isothermic bath.

The pressure to which a chemical reaction is performed may also be a parameter to adjust. For instance, a reaction between the tetrakishydroxymethyl phosphonium salt(s) and the base(s) may be performed at a pressure of 0.5 to 1.5 bar, preferably 0.6 to 0.8 bar. The pressure of the reaction may be controlled and adjusted by any means known in the art. For example, the pressure in the first reaction chamber may be controlled and adjusted using a pressure sensor connected to a membrane pump of suitable strength and capacity, leading to an exhaust, in a manner similar to the one applied in the rotatory evaporator technology.

The reaction between tetrakishydroxymethyl phosphonium salt(s) and the base(s) yields a mixture of trishydroxymethyl phosphine and formaldehyde.

According to one embodiment, the formaldehyde may be removed from the mixture of trishydroxymethyl phosphine and formaldehyde during the formation of this mixture.

According to another embodiment, the formaldehyde may be removed from the mixture of trishydroxymethyl phosphine and formaldehyde after the formation of this mixture.

The removing of the formaldehyde allows advantageously the obtaining of a THP which is pure and stable.

According to one embodiment, the formaldehyde may be removed from the mixture of trishydroxymethyl phosphine and formaldehyde during and/or after the formation of this mixture.

The formaldehyde may be removed from the mixture of trishydroxymethyl phosphine and formaldehyde while the mixture is still in the first reaction chamber and/or from the mixture at the outlet of the first reaction chamber, and/or after having moved the mixture from the first reaction chamber into another chamber.

According to an embodiment, the formaldehyde is removed by bubbling an inert gas through the mixture of trishydroxymethyl phosphine and formaldehyde. The bubbling may be carried out in the first reaction chamber and/or at the outlet of the chamber.

Preferably, said inert gas may be nitrogen or argon, or $CO_2$, or even dry air, in particular nitrogen or argon.

The bubbling of a gas within the mixture of trishydroxymethyl phosphine and formaldehyde may be carried out by any means known in the art. For example, the bubbling may be carried out by releasing the gas from a bottle under pressure through a suitable nozzle or gas distributor known in the industry.

According to another embodiment, the formaldehyde is removed by placing the mixture of trishydroxymethyl phosphine and formaldehyde under reduced pressure.

The reducing of the pressure may be carried out by any means known in the art. For example, the reducing of the pressure may be carried out by a membrane or pump of other type, of suitable strength and capacity.

The exhaust stream of the pump that contains formaldehyde can be immersed in a scrubbing solution, that can either dissolve formaldehyde and produce a formaldehyde solution, or that contains an oxidant that will oxidize formaldehyde to $CO_2$ and water. As an oxidant there are many suitable reagents, for example hydrogen peroxide, peroxoacetic acid, peroxosulfuric acid, peroxobenzoic acid, solid peroxides, potassium permanganate, potassium chromate or potassium dichromate.

Solutions of tetrakishydroxymethyl phosphonium salt(s) and of base(s) may be driven into the first reaction chamber using pumps, such as gear pumps, membrane pumps or peristaltic pumps.

According to one embodiment, the tetrakishydroxymethyl phosphonium salt(s) and the base(s) can be simultaneously fed into the first reaction chamber.

According to another embodiment, the tetrakishydroxymethyl phosphonium salt(s) and the base(s) may be sequentially fed into the first reaction chamber.

A first reaction chamber which may be used within a method of the invention may comprise at least one inlet and at least one outlet.

A pump may be connected to the inlet(s). A pump may also be connected to the outlet(s).

In one embodiment, the first reaction chamber may comprise one inlet, and the mixture of the tetrakishydroxymethyl phosphonium salt(s) and the base(s) may be carried out at a point before the entry into the reaction chamber by means of a T-junction. A T-junction may comprise at least two entries points and one exit point. In one embodiment, a T-junction may comprise a number of entries points equal to the number of compounds to bring into the chamber and one exit point.

In another embodiment, the first reaction chamber may comprise at least two inlets, and preferably a number of inlets equal to the number of compounds to bring into the chamber. Each of the tetrakishydroxymethyl phosphonium salt(s) and the base(s) may be conveyed into the first reaction chamber by means of an inlet. The mixture of the tetrakishydroxymethyl phosphonium salt(s) and the base(s) may be carried out into the reaction chamber.

According to one embodiment, a first reaction chamber may be connected to another reaction chamber or to a plurality of reaction chambers. When a first reaction chamber is connected to a plurality of reaction chambers, those additional reaction chambers may be configured in a serial or in a parallel manner. Preferably, those additional reaction chambers may be configured in a serial manner.

According to a preferred embodiment, a first reaction chamber may be connected to at least a second reaction chamber.

The additional chamber may comprise inlet(s) and outlet(s) as above-described for the first reaction chamber.

In order to feed a second reaction chamber, the THP obtained in the first reaction chamber may be introduced in the second reaction chamber by means of a pump, in particular such as above described. The first and second chambers may be connected by means of suitable tubing connecting the outlet of the first chamber to the inlet(s) of the second chambers.

A method of the invention may be carried out in a continuous-flow reactor or in a micro-reactor.

In a micro-reactor, reaction chambers are configured as channels, for example embedded into a support.

In particular, a micro-reactor suitable for the invention may comprise at least one channel having a cross-section area ranging from 1 mm$^2$ to 1 cm$^2$.

For example, a continuous-flow reactor suitable for the invention may comprise two entry points, a static mixer or T-junction, a fixed volume and one exit point.

According to one embodiment, the THP may be collected at the outlet of the first reaction chamber by directing the outlet into suitable bottles, or, into a collection tank.

The THP thus obtained may be stored for further use at a later point in time. Alternatively, when the first reaction chamber is connected to a plurality of reaction chambers, and preferably to a second reaction chamber, the THP may be subsequently and directly reacted with other reactive agents to give a variety of phosphorus compounds.

In one embodiment of the invention, the THP may be used to prepare trialkyl phosphines.

According to another embodiment of the invention, the THP may be used to prepare trialkyl phosphines based polymers.

According to another embodiment, the THP may be used to prepare polymer of alkyl phosphines on resin or polymer beads.

According to one embodiment, a method according to the invention may comprise at least additional subsequent steps consisting of feeding a second reaction chamber with, from one hand, the trishydroxymethyl phosphine and, from another hand, at least one reactant, under conditions suitable for a reaction of said trishydroxymethyl phosphine with said reactant(s) to form a trialkylphosphine; and isolating said trialkylphosphine.

A reactant suitable for the invention is a nucleophilic reactant and may comprise one reactive site liable to react with the THP. A reactive site suitable for the invention may be in particular chosen from "NH" or "OH".

According to a preferred embodiment, a reactant suitable for the invention may be chosen from ammonia, primary amines, secondary amines, urea and its derivatives containing at least one NH moiety, thiourea and its derivatives containing at least one NH moiety or amino acids.

Following its recovery from the first reaction chamber, the THP may be diluted in an aqueous solvent, and preferably water, or concentrated by evaporation.

The THP may also be diluted in alcohols, such as ethanol, ethyleneglycol, methanol, 1-propanol, 2-propanol, glycerol, and their higher analogues up to pentanol, or in dimethylsulfoxide, dimethylformamide, dimethylacetamide, tetrahydrofurane.

In the second reaction chamber, the THP may be introduced at a concentration ranging from 2 mol/l to 4 mol/l.

A reactant suitable for the subsequent steps of the invention may be preferably solubilized into an aqueous solvent, and more preferably in water or in alcohols, such as ethanol, ethyleneglycol, methanol, 1-propanol, 2-propanol, glycerol, and their higher analogues up to pentanol, or in dimethylsulfoxide, dimethylformamide, dimethylacetamide, tetrahydrofurane.

The reaction of the trishydroxymethyl phosphine with the reactant(s) to form a trialkylphosphine may be performed at a temperature ranging from 0° C. to 100° C.

The time of residence of the THP and the reactant(s) in the second reaction chamber may range from 1 to 30 minutes.

The reaction of the trishydroxymethyl phosphine with the reactant(s) to form a trialkylphosphine may be carried out at a pressure ranging from 0.5 to 5 bar.

The reaction of the trishydroxymethyl phosphine with the reactant(s) to form a trialkylphosphine may be carried out at a pH ranging from 6.5 to 7.5.

The means used to control and adjust the temperature, pressure and pH of the reaction between the trishydroxymethyl phosphine with the reactant(s) to form a trialkylphosphine may be as above-described for the reaction carried out in the first reaction chamber.

The trialkylphosphine obtained by reacting the trishydroxymethyl phosphine with the reactant(s) may be isolated and recovered by any means and techniques known in the art. In particular, the trialkylphosphine may be isolated by extraction into an organic solvent immiscible with water such as diethylether, toluene, petroleum ether or dichloromethane, if the product phosphine is solid soluble in organic solvent. If the product is liquid, (fractional) distillation could be used to isolate it. As a final purification step, either crystallization from a suitable solvent or column chromatography are the standard methods.

According to one embodiment, a method according to the invention may comprise at least additional subsequent steps consisting of feeding a second reaction chamber with, from one hand, the trishydroxymethyl phosphine and, from another hand, at least one reactant, under conditions suitable for a reaction of said trishydroxymethyl phosphine with said reactant(s) to form a polymer product; and isolating said polymer product.

A reactant suitable for the invention is a nucleophile reactant and may comprise at least two reactive sites, each liable to react with the THP. A reactive site suitable for the invention may be in particular chosen from "NH" or "OH". According to an embodiment, the two requested reactive sites may be borne in one nucleophile moiety or may be borne in two distinct nucleophilic moieties. A nucleophile moiety may comprise at least one reactive site, preferably two reactive sites, more preferably three and more preferably four reactive sites.

According to a preferred embodiment, a reactant suitable for the invention may be chosen from ammonia, an ammonium containing compound, or a primary amine containing compound, and preferably is ammonia.

A reactant suitable for the invention may be chosen from:
an ammonium containing compound, such as $NH_4OH$ or $NH_4Cl$;
a primary amine containing compound, such as $NHR^aR^b$ with $R^a$ and $R^b$, identical or different, representing
H;
linear, branched, or cyclic ($C_1$-$C_{25}$)alkyl groups, optionally substituted with at least one moiety selected from the group consisting of —$NH_2$, —C(O)OH, —OH, —C(O)$NH_2$, in which $R^c$ is H or $CH_3$, a saturated, unsaturated or aromatic hydrocarbon-based 5 to 9 membered-mono- or bi-cycle comprising optionally at least one heteroatom chosen from N, O or S;
—C(O)$R^d$ or —C(S)$R^d$ with $R^d$ being $NH_2$ or a linear, branched or cyclic $C_1$-$C_2$ alkyl optionally substituted with at least one —$NH_2$ moiety;

with x ranging from 2 to 70;

with y ranging from 2 to 40 and x+z ranging from 1 to 6;

with x being 2 or 3;

with R being H or Et, n being 0 or 1 and x+y+z ranging from 5 to 90;
a primary amine containing compound, such as $NH_2$—R—$NH_2$, $NH(R)$—R—$NH_2$, $NH(R)$—R—$NH(R)$ with R, identical or different, representing a $C_1$-$C_{30}$ alkyl, alkoxy or alkylene group, optionally substituted with —OH or —$NH_2$, or a $C_5$-$C_{30}$ aryl or arylene group.

According to a preferred embodiment, a reactant suitable for the invention may be ammonia.

Preferably, the subsequent steps of a method of the invention may be continuously carried out.

Following its recovery from the first reaction chamber, the THP may be diluted in an aqueous solvent, and preferably water, or concentrated by evaporation.

The THP may also be diluted in alcohols, such as ethanol, ethyleneglycol, methanol, 1-propanol, 2-propanol, glycerol, and their higher analogues up to pentanol, or in dimethylsulfoxide, dimethylformamide, dimethylacetamide, tetrahydrofurane.

In the second reaction chamber, the THP may be introduced at a concentration ranging from 1 mol/l to 5 mol/l.

A reactant suitable for the subsequent steps of the invention may be preferably solubilized into an aqueous solvent, and more preferably in water, or in alcohols, such as ethanol, ethyleneglycol, methanol, 1-propanol, 2-propanol, glycerol, and their higher analogues up to pentanol, or dimethylsulfoxide, dimethylformamide, dimethylacetamide, tetrahydrofurane.

In the second reaction chamber, the reactant(s) may be introduced at a concentration ranging from 1 mol/l to 5 mol/l.

The reaction of the trishydroxymethyl phosphine with the reactant(s) to form a polymer product may be performed at a temperature ranging from 20° C. to 80° C.

The time of residence of the THP and the reactant(s) in the second reaction chamber may range from 1 to 30 minutes.

The reaction of the trishydroxymethyl phosphine with the reactant(s) to form a polymer product may be carried out at a pressure ranging from 0.7 bar to 5 bar.

The reaction of the trishydroxymethyl phosphine with the reactant(s) to form a polymer product may be carried out at a pH ranging from 6.0 to 7.0.

The means used to control and adjust the temperature, pressure and pH of the reaction between the trishydroxymethyl phosphine with the reactant(s) to form a polymer product may be as above-described for the reaction carried out in the first reaction chamber.

The polymer product obtained by reacting the trishydroxymethyl phosphine with the reactant(s) may be isolated and recovered by any means and techniques known in the art. In particular, the polymer product may be isolated by precipitation and the filtration of the resulting solid polymer, or by solvent evaporation up to the gel formation point and collection of the gelatinous product by decantation of the remaining liquid.

In another embodiment of the invention, the phosphine can be used to functionalize a solid support, such as resin or polymer beads. The functionalized solid support may be further modified by in situ forming a polymer. These resulting polymers and functionalized materials can interact selectively with transition metals and find applications, among others, in water treatment.

In one embodiment, a method of the invention may comprise at least subsequent steps consisting of:
  feeding a second reaction chamber with, from one hand, said trishydroxymethyl phosphine and, from another hand, resin beads comprising at least one "NH" reactive function, under conditions suitable for a reaction of said trishydroxymethyl phosphine with said "NH" reactive function(s), to form bishydroxymethyl phosphine functionalized resin beads; and
  isolating said bishydroxymethyl phosphine functionalized resin beads.

Following its recovery from the first reaction chamber, the THP may be diluted in an aqueous solvent, and preferably water, or concentrated by evaporation.

The THP may also be diluted in alcohols, such as ethanol, ethyleneglycol, methanol, 1-propanol, 2-propanol, glycerol, and their higher analogues up to pentanol, or in dimethylsulfoxide, dimethylformamide, dimethylacetamide, tetrahydrofurane.

In the second reaction chamber, the THP may be introduced at a concentration ranging from 2 mol/l to 4 mol/l.

Resin beads comprising at least one "NH" reactive function suitable for the subsequent steps of the invention may be preferably suspended or dispersed into an aqueous solvent, and more preferably in water, or in alcohols, such as ethanol, ethyleneglycol, methanol, 1-propanol, 2-propanol, glycerol, and their higher analogues up to pentanol, or dimethylsulfoxide, dimethylformamide, dimethylacetamide, tetrahydrofurane.

In the second reaction chamber, the resin beads comprising at least one "NH" reactive function(s) may be introduced at a concentration ranging from 80 vol % to 50 vol %.

The reaction of the trishydroxymethyl phosphine with the resin beads comprising at least one "NH" reactive function (s) to form bishydroxymethyl phosphine functionalized resin beads may be performed at a temperature ranging from 20° C. to 80° C.

The time of residence of the THP and the reactant(s) in the second reaction chamber may range from 1 to 30 minutes.

The reaction of the trishydroxymethyl phosphine with the resin beads comprising at least one "NH" reactive function (s) to form bishydroxymethyl phosphine functionalized resin beads may be carried out at a pressure ranging from 0.7 bar to 5 bar.

The reaction of the trishydroxymethyl phosphine with the resin beads comprising at least one "NH" reactive function (s) to form bishydroxymethyl phosphine functionalized resin beads may be carried out at a pH ranging from 6.0 to 7.0.

The means used to control and adjust the temperature, pressure and pH of the reaction between the trishydroxymethyl phosphine with the resin beads comprising at least one "NH" reactive function(s) to form bishydroxymethyl phosphine functionalized resin beads may be as above-described for the reaction carried out in the first reaction chamber.

The bishydroxymethyl phosphine functionalized resin beads obtained by reacting the trishydroxymethyl phosphine with the resin beads comprising at least one "NH" reactive function(s) may be isolated and recovered by any means and techniques known in the art. In particular, the bishydroxymethyl phosphine functionalized resin beads may be isolated by filtration using any kind of filtration means with mesh sizes of 0.1 to 0.4 mm.

This method may further comprise at least subsequent steps consisting of:
feeding a third reaction chamber with, from one hand, said bishydroxymethyl phosphine functionalized resin beads and, from another hand, with a nucleophile reactive agent, to form in situ a phosphorus containing polymeric chain grafted on said beads, said nucleophile reactive agent being of formula $NHR^aR^b$, wherein $R^a$ and $R^b$ are, independently of each other, selected from the group consisting of:

H;

linear, branched, or cyclic ($C_1$-$C_{25}$)alkyl groups, optionally substituted with at least one moiety selected from the group consisting of $-NH_2$, $-C(O)OH$, $-OH$, $-C(O)NH_2$, $-SR^c$ in which $R^c$ is H or $CH_3$, a saturated, unsaturated or aromatic hydrocarbon-based 5 to 9 membered-mono- or bi-cycle comprising optionally at least one heteroatom chosen from N, O or S;

$-C(O)R^d$ or $-C(S)R^d$ with $R^d$ being $NH_2$ or a linear, branched or cyclic $C_1$-$C_{25}$ alkyl optionally substituted with at least one $-NH_2$ moiety;

with x ranging from 2 to 70;

with y ranging from 2 to 40 and x+z ranging from 1 to 6;

with x being 2 or 3;

with R being H or Et, n being 0 or 1 and x+y+z ranging from 5 to 90; and isolating the resin beads bearing a phosphorus containing polymeric chain.

Following its recovery from the second reaction chamber, the bishydroxymethyl phosphine functionalized resin beads may be suspended or dispersed in an aqueous solvent, and preferably water, or in alcohols, such as ethanol, ethyleneglycol, methanol, 1-propanol, 2-propanol, glycerol, and their higher analogues up to pentanol, or dimethylsulfoxide, dimethylformamide, dimethylacetamide, tetrahydrofurane. In the third reaction chamber, the bishydroxymethyl phosphine functionalized resin beads may be introduced at a concentration ranging from 80 to 50 vol %.

A reactant suitable for the subsequent steps of the invention may be preferably solubilized into an aqueous solvent, and more preferably in water, or in alcohols, such as ethanol, ethyleneglycol, methanol, 1-propanol, 2-propanol, glycerol, and their higher analogues up to pentanol, or dimethylsulfoxide, dimethylformamide, dimethylacetamide, tetrahydrofurane.

In the third reaction chamber, the reactant(s) may be introduced at a concentration ranging from 2 to 5 mol/l.

The reaction of the bishydroxymethyl phosphine functionalized resin beads with the reactant(s) to form resin beads bearing a phosphorus containing polymeric chain may be performed at a temperature ranging from 20° C. to 80° C.

The time of residence of the THP and the reactant(s) in the second reaction chamber may range from 1 to 30 minutes.

The reaction of the bishydroxymethyl phosphine functionalized resin beads with the reactant(s) to form resin beads bearing a phosphorus containing polymeric chain may be carried out at a pressure ranging from 0.7 bar to 5 bar.

The reaction of the bishydroxymethyl phosphine functionalized resin beads with the reactant(s) to form resin beads bearing a phosphorus containing polymeric chain may be carried out at a pH ranging from 6.0 to 7.0.

The means used to control and adjust the temperature, pressure and pH of the reaction between the bishydroxymethyl phosphine functionalized resin beads with the reactant(s) to form resin beads bearing a phosphorus containing polymeric chain may be as above-described for the reaction carried out in the first reaction chamber.

The resin beads bearing a phosphorus containing polymeric chain obtained by reacting the bishydroxymethyl phosphine functionalized resin beads with the reactant(s) may be isolated and recovered by any means and techniques known in the art. In particular, the resin beads bearing a phosphorus containing polymeric chain may be isolated by filtration using any kind of filtration means with mesh sizes of 0.1 to 0.4 mm.

A liquid waste can be harvested at the outlet of the second and/or third reaction chamber(s), and, according to the case, fed back in the second reaction or third reaction chamber(s).

Preferably, a method of the invention may be continuously performed.

The present invention will be better understood by referring to the following examples and figures which are provided for illustrative purpose only and should not be interpreted as limiting in any manner the present invention.

EXAMPLES

Example 1

Example According to the Invention (Removal of Formaldehyde Using Various Means)

Figure 1:
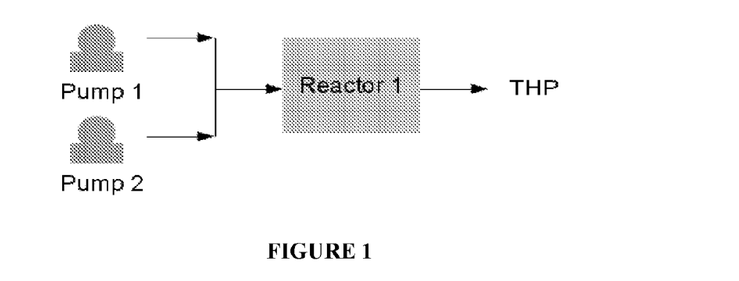
FIG. 1: Schematic representation of a method of preparation of THP in one step, as illustrated in examples 1 and 2.

A solution of THPS (65-75% in water) and a solution of NaOH (Sodium hydroxide) (1.0 M) were prepared. As illustrated in FIG. 1, using gear pumps, the solutions were pumped into a flow-reactor comprising two entry points, a static mixer, a fixed volume and one exit point.

The internal volume of the reactor and the flow rate of the pumps were adjusted such that a residence time between 1 and 5 minutes is ensured.

The pumps were set to flow-rates such that the pH after the reaction was between 6.5 and 7.0, and not over 7.1. The reactor was kept at a constant temperature by submersion in an externally cooled isothermic bath.

At the entrance and the exit of the reactor, samples were taken to measure $^{31}P$ NMR and FT-IR spectra:
$^{31}P$ NMR of starting material: d=25 ppm (THPS);
$^{31}P$ NMR of product: d=−25 ppm (THP);
FT-IR: two unresolved bands at 1090 (strong) and 1040 (medium) $cm^{-1}$.

The yield was high. The results showed formation of THP only. There was no THPO formation. Indeed, NMR (Nuclear Magnetic Resonance) and FT-IR (Fourier Transform Infra-Red) data indicated the clean formation of THP. The oxide of THP, THPO, normally displays a characteristic intense band at 1100-1110 $cm^{-1}$, which did not appear in the FT-IR spectra. According to IR and ICP-OES, the concentration of THP obtained in this way was 2.5 mol/l.

The produced THP was collected in a recipient equipped with a connection for a membrane pump, and an exhaust tube with a valve, leading to the fume hood exhaust.

In a series of experiments, this setup was used for:
- according to a first option: the continuous formaldehyde removal by means of bubbling of an inert gas such as argon or nitrogen gently through the incoming solution of THP.
- according to a second option: the continuous formaldehyde removal by means of applying slight underpressure of 600-700 mbar, using the connected membrane pump.

Figure 2:
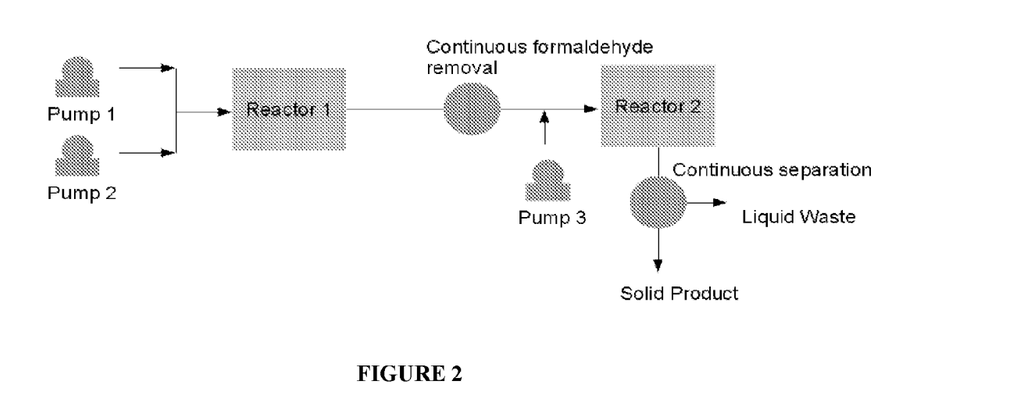
FIG. 2: Schematic representation of a method of preparation of THP according to the invention, according to example 1.

The THP obtained in these experiments was used immediately for reaction with ammonia and production of a powder polymer in the setup schematically represented in the FIG. 2 according to the following procedure.

The purified THP was then reacted with ammonia introduced by pump 3 and a polymer product was formed in reactor 2. The concentrations of the reactants were both 2.5 mol/l, the mixing was ensured by the turbulent flow in the tube reactor. The pH value was between 6.0 and 7.0, while the total residence time in the reactor was 12 minutes.

The product of the polymerization was isolated using a continuous liquid/solid separation apparatus consisting of two chambers. The first chamber is used for collection of the liquid that was obtained by the filtration of the reaction mixture over a flat filter on top of the chamber one. The solid product collected on the flat filter was scooped from the filter and conveyed into the second chamber, where it was collected as fine white powder.

In the liquid fraction, there was no unreacted THP, according to the FT-IR, while only a small amount of phosphorus was detected by ICP-OES (50-200 mg/l, which is below 0.5% of the starting phosphorus amount: 2.5 mol/l equals 77500 mg/l).

Thus, the polymer formation is achieved with >99% yield based on the amount of used THP.

The product obtained in both options, whose procedure included the active removal of formaldehyde, was heated for 30 minutes at 60° C. No changes were observed to the thus formed products and no further reactions leading to PTA as a final product where observed, demonstrating that formaldehyde was efficiently removed and demonstrating that the THP produced in this way can be used for further syntheses without risk of having formaldehyde-caused side reactions.

Example 2

Comparative Example of Example 1

The same procedure as example I is performed to produce THP.

However, instead of removing formaldehyde, the setup was used for nothing, i.e. it was just left open to the fume hood exhaust without actively removing formaldehyde.

Here, the formaldehyde is largely retained in the solution and, as show below; it leads to the formation of side-products in the subsequent reactions.

As in example 1, the THP was used immediately for reaction with ammonia and production of a powder polymer in the setup schematically represented in the FIG. 2 according to the procedure specified in example 1.

In this experiment, with the produced THP which was contaminated by formaldehyde, the solid polymer product was contaminated by formaldehyde, too, what had grave consequences for the stability of the polymer.

The main side reaction occurring when formaldehyde is present is the conversion of the polymeric product into a gelatinous product PTA (1,3,5-triaza-7-phosphaadamantane) upon heating the polymer, what was readily observed when the product was heated for 30 minutes at 60° C. Almost all of the polymeric powder was converted to a translucent gelatinous mass, demonstrating the presence of a large amount of formaldehyde.

Example 3

Comparative Example: Synthesis of THP from THPS in an Aqueous Batch Reaction 10 g of THPS is neutralized through dropwise addition of 25 ml of NaOH at 1.5 M while the solution is stirred. After the addition was complete, the reaction was left for another 5 minutes and a $^{31}P$ NMR spectrum was measured:
$^{31}P$ NMR of starting material: d=25 ppm (THPS);
$^{31}P$ NMR of product: d=+49 ppm (THPO), −25 ppm (THP).

The $^{31}P$ NMR spectrum shows a major peak at 49 ppm.

The yield of THP was low (about 60%) due to significant THPO formation, according to the NMR and FT-IR data.

Example 4

Comparative Example: Synthesis of THP from THPC Under Inert Atmosphere (Procedure According to Pringle et al., Platinum Metals Rev, 1990, 34, 2, 74)

THPC (80% in water) was dried under reduced pressure, where the water was removed through co-evaporation with toluene (4×), recrystalized from isopropanol at 4° C. overnight, filtered, washed and dried under nitrogen atmosphere.

The crystals were then dissolved in methoxylithium (MeOLi) (1M in Methanol) at room temperature under nitrogen. After 10 min a $^{31}$P NMR spectrum was taken showing a clean conversion of the THPC to THP:
$^{31}$P NMR of starting material: d=25 ppm (THPS);
$^{31}$P NMR of product: d=−25 ppm (THP).

The yield was high but the procedure is complicated. Whether the final product is THP or a derivative of THP, the final yield will be directly related to the formation (or the lack thereof) of THPO. Clearly, in this example, the yield of the continuous-flow reaction was close to equal to 100% whereas the batch reaction was no higher than 60%. The batch performed under inert atmosphere is not relevant to scale-up.

Example 5

Example According to the Invention: Reaction of Continuously Produced THP with Polymer Resin Beads and Subsequent Isolation of Unreacted THP Using the same experimental setup as Example 1, where pump 3 is used to inject amine funtionalized polymer beads, THP funtionalized resin is made.

The whole installation is placed under slight under pressure, so that the gaseous formaldehyde, which represents both a health hazard and a possible initiator of side reactions, was efficiently and continuously removed from the system.

To a stream of 20 l/h total volumetric flow and 48 mol/h molar flow of THP flowing out of reactor 1, a stream of 32 l/h volumetric flow containing a suspension of resin beads and water in the respective ratio of 4:1 is mixed. This mixture is led through a microfluidic tube reactor of such length as to ensure the reaction/residence time of 15 minutes (reactor 2). At the exit of the reactor the suspension is separated in a liquid/solid separation unit, with the liquid stream bearing 10 mol/h of unreacted THP (concentration of THP 0.4 mol/l). Under such conditions, the consumption of THP is at 79% with respect to the initial amount. At the same time, the content of the phosphorus loaded on the resin high at about 1.3 mol/l. The IR data of the solid product displayed bands typical for THP, at slightly shifted positions from the parent THP: a strong band at 1045 cm$^{-1}$, and a shoulder of weaker intensity at 1097 cm$^{-1}$.

The yield of THP was high which allows its high utilization.

Indeed, given the high purity of this THP, it can be used for other purposes. For example, it can be reacted with ammonia to give an insoluble polymer in quantitative yield. It can also be re-injected in the reactor, for example instead of water to transport the resin beads of the above sample. This further increases the overall efficiency of the reactions. Such re-use of unreacted THP is only possible if the THP is pure and stable, as is the case with the current invention.

The invention claimed is:

1. A method for preparing trishydroxymethyl phosphine from tetrakishydroxymethyl phosphonium salt, said method comprising at least the steps of:
   continuously feeding a first reaction chamber with, from one hand, at least one tetrakishydroxymethyl phosphonium salt and, from another hand, at least one base, under conditions suitable for a reaction of said tetrakishydroxymethyl phosphonium salt(s) with said base(s), at a pH ranging from 6.5 to 7.5, to form a mixture of trishydroxymethyl phosphine and formaldehyde; and
   continuously removing said formaldehyde.

2. The method according to claim 1, wherein said formaldehyde is removed during the formation of said mixture of trishydroxymethyl phosphine and formaldehyde and/or after the formation of said mixture of trishydroxymethyl phosphine and formaldehyde.

3. The method according to claim 1, wherein said formaldehyde is removed by bubbling an inert gas through said mixture of trishydroxymethyl phosphine and formaldehyde.

4. The method according to claim 3, wherein said inert gas is nitrogen, argon, $CO_2$, or dry air.

5. The method according to claim 1, wherein said formaldehyde is removed by placing said mixture of trishydroxymethyl phosphine and formaldehyde under reduced pressure.

6. The method according to claim 1, wherein said tetrakishydroxymethyl phosphonium salt(s) and said base(s) are simultaneously fed into said first reaction chamber.

7. The method according to claim 1, wherein said reaction is brought to a pH ranging from 6.9 to 7.0.

8. The method according to claim 1, wherein said base(s) is/are chosen from NaOH, $CaCO_3$, KOH, $Na_2CO_3$, CaO, $Ca(OH)_2$, and non-nucleophilic amines.

9. The method according to claim 1, wherein said first reaction chamber is a continuous-flow reactor or a micro-reactor.

10. The method according to claim 9, wherein the micro-reactor is a micro-reactor comprising at least one channel having a cross-section area ranging from 1 mm$^2$ to 1 cm$^2$.

11. The method according to claim 1, comprising at least subsequent steps consisting of:
   feeding a second reaction chamber with, from one hand, said trishydroxymethyl phosphine and, from another hand, at least one reactant, under conditions suitable for a reaction of said trishydroxymethyl phosphine with said reactant(s) to form a polymer product; and
   isolating said polymer product.

12. The method according to claim 11, wherein said reactant(s) is/are chosen from ammonia, an ammonium containing compound, or a primary amine containing compound.

13. The method according to claim 11, said method being continuously performed.

14. The method according to claim 1, comprising at least subsequent steps consisting of:
   feeding a second reaction chamber with, from one hand, said trishydroxymethyl phosphine and, from another hand, resin beads comprising at least one "NH" reactive function, under conditions suitable for a reaction of said trishydroxymethyl phosphine with said "NH" reactive function(s), to form bishydroxymethyl phosphine functionalized resin beads; and
   isolating said bishydroxymethyl phosphine functionalized resin beads.

15. The method according to claim 14, comprising at least subsequent steps consisting of:
   feeding a third reaction chamber with, from one hand, said bishydroxymethyl phosphine functionalized resin beads and, from another hand, with a nucleophile reactive agent, to form in situ a phosphorus containing polymeric chain grafted on said beads, said nucleophile reactive agent being of formula NHR$^a$R$^b$, wherein R$^a$ and R$^b$ are, independently of each other, selected from the group consisting of:

H;

linear, branched, or cyclic (C$_1$-C$_{25}$)alkyl groups, optionally substituted with at least one moiety selected from the group consisting of —NH$_2$, —C(O)OH, —OH, —C(O)NH$_2$, —SR$^c$ in which R$^c$ is H or CH$_3$, a saturated, unsaturated or aromatic hydrocarbon-based to 9 membered-mono- or bi-cycle comprising optionally at least one heteroatom chosen from N, O or S;

—C(O)R$^d$ or —C(S)R$^d$ with R$^d$ being NH$_2$ or a linear, branched or cyclic C$_1$-C$_{25}$ alkyl optionally substituted with at least one —NH$_2$ moiety;

with x ranging from 2 to 70;

with y ranging from 2 to 40 and x+z ranging from 1 to 6;

with x being 2 or 3;

with R being H or Et, n being 0 or 1 and x+y+z ranging from 5 to 90; and isolating the resin beads bearing a phosphorus containing polymeric chain.

16. The method according to claim 14, wherein a liquid waste is harvested and fed back in said second reaction chamber.

17. The method according to claim 14, wherein said method is continuously performed.

* * * * *